(12) United States Patent
Tornier

(10) Patent No.: US 8,317,835 B2
(45) Date of Patent: Nov. 27, 2012

(54) HINGE MOUNTING SYSTEM FOR A SPINAL OSTEOSYNTHESIS DEVICE

(75) Inventor: Alain Tornier, Saint-Ismier (FR)

(73) Assignee: Clariance, Dainville (FR)

( * ) Notice: Subject to any disclaimer, the term of this patent is extended or adjusted under 35 U.S.C. 154(b) by 247 days.

(21) Appl. No.: 12/645,074

(22) Filed: Dec. 22, 2009

(65) Prior Publication Data

US 2010/0160979 A1 Jun. 24, 2010

Related U.S. Application Data

(60) Provisional application No. 61/139,923, filed on Dec. 22, 2008.

(30) Foreign Application Priority Data

Dec. 19, 2008 (FR) ...................................... 08 07171

(51) Int. Cl.
*A61B 17/70* (2006.01)
(52) U.S. Cl. ..................................................... 606/265
(58) Field of Classification Search .................. 606/246, 606/264, 274, 275, 277, 278, 279; 403/70–71, 403/159, 233–235, 290, 336–338
See application file for complete search history.

(56) References Cited

U.S. PATENT DOCUMENTS

| 5,090,833 | A | * | 2/1992 | Oertle et al. ..................... 403/12 |
| 5,662,653 | A | | 9/1997 | Songer et al. |
| 5,876,403 | A | * | 3/1999 | Shitoto ......................... 606/308 |
| 5,935,133 | A | * | 8/1999 | Wagner et al. ................. 606/103 |
| 7,909,852 | B2 | * | 3/2011 | Boomer et al. ................ 606/246 |
| 2003/0050640 | A1 | | 3/2003 | Lee et al. |
| 2008/0065079 | A1 | | 3/2008 | Bruneau et al. |

FOREIGN PATENT DOCUMENTS

WO 2007/041265 A 4/2007

OTHER PUBLICATIONS

European Search Report in Corresponding Application FA 716836 and FR 0807171 Dated Apr. 6, 2009.

* cited by examiner

*Primary Examiner* — Anu Ramana
(74) *Attorney, Agent, or Firm* — Young & Thompson

(57) ABSTRACT

The hinge mounting system according to the present invention is constituted of a link connector (10) comprising, on either side of a U-shaped opening (8), a first and a second vertical branch (11, 12) respectively cooperating through axes of rotation (13, 14) with a clamping element (15) enabling the linking rod (4) to be immobilized in translation and in rotation after it has been pivoted and locked above the opening (8) by a lock (16) elastically loaded by a leaf spring (29).

9 Claims, 5 Drawing Sheets

HINGE MOUNTING SYSTEM FOR A SPINAL OSTEOSYNTHESIS DEVICE

FIELD OF THE INVENTION

The present invention relates to a hinge mounting system for a spinal osteosynthesis device and more particularly to a system for fixing and immobilizing a linking rod inside a connector or in the head of a pedicle screw that was previously anchored in a vertebra of a spinal segment to be instrumented.

BACKGROUND OF THE INVENTION

Various mounting systems are known allowing the immobilization in translation and in rotation of a linking rod inside a connector or in the head of a pedicle screw anchored in a vertebra of a spinal segment to be instrumented.

In each mounting system, it is noted that all of the independent pieces that must be assembled by the surgeon have small sizes, making assembly on the site delicate and difficult.

OBJECT OF THE INVENTION

The object of the mounting system according to the present invention is to prevent the assembly of pieces between each other while allowing the linking rod to be simply and quickly placed inside the connector or in the head of the previously anchored pedicle screw.

Also, the hinge mounting system according to the present invention is capable of being mounted on any osseous anchoring means of a spinal osteosynthesis device such as, for example, on an anchoring screw head, or on a polyaxial screw or hook connector.

SUMMARY OF THE INVENTION

The mounting system according to the present invention is constituted of a link connector comprising on either side of a U-shaped opening a first and second vertical branch respectively cooperating through axes of rotation with a clamping element allowing the immobilization in translation and in rotation of a linking rod after it has been pivoted and locked above the opening by a lock that has been elastically loaded by a leaf spring.

The mounting system according to the present invention comprises a clamping element that is traversed in its middle by a threaded bore cooperating with a locking screw allowing the linking rod to be immobilized in translation and in rotation.

The mounting system according to the present invention comprises a clamping element comprising an edge in which hook-shaped notches, separated by a central and vertical groove, are arranged.

The mounting system according to the present invention comprises a link connector whose second branch comprises, along a vertical direction, a groove allowing, on the one hand, the placement and guiding of the lock around the axis of rotation and, on the other hand, the mounting of the leaf spring on which said lock is supported.

The mounting system according to the present invention comprises a lock, opposite a bore receiving the axis of rotation, that is integral with locking fingers.

The mounting system according to the present invention comprises a lock comprising a vertical flat surface that extends inside a groove so as to retain the free end of the leaf spring opposite from the end that is integral with said link connector.

The mounting system according to the present invention comprises a link connector wherein the axes of rotation ensuring pivoting of the clamping element and of the lock are offset in relation to one another.

The mounting system according to the present invention comprises a link connector that is integral with an osseous anchoring element constituted of an osseous anchoring screw.

The mounting system according to the present invention comprises a link connector that is integral with an osseous anchoring element constituted of a hook.

The mounting system according to the present invention comprises a link connector that is mounted on an osseous anchoring element constituted of an osseous anchoring screw with a spherical head.

BRIEF DESCRIPTION OF THE DRAWINGS

The attached drawings, given by way of example, allow the invention, the characteristics that the invention presents and the advantages that the invention is likely to obtain to be better understood:

FIGS. 1 to 4 show an osseous anchoring element 1 constituted, for example, of an osseous anchoring screw 2 of a spinal osteosynthesis device 3 allowing the mounting and immobilization in translation and in rotation of a linking rod 4 connecting different vertebral stages of a spinal segment from a vertebral column to be instrumented.

DETAILED DESCRIPTION OF THE INVENTION

Figure 1:
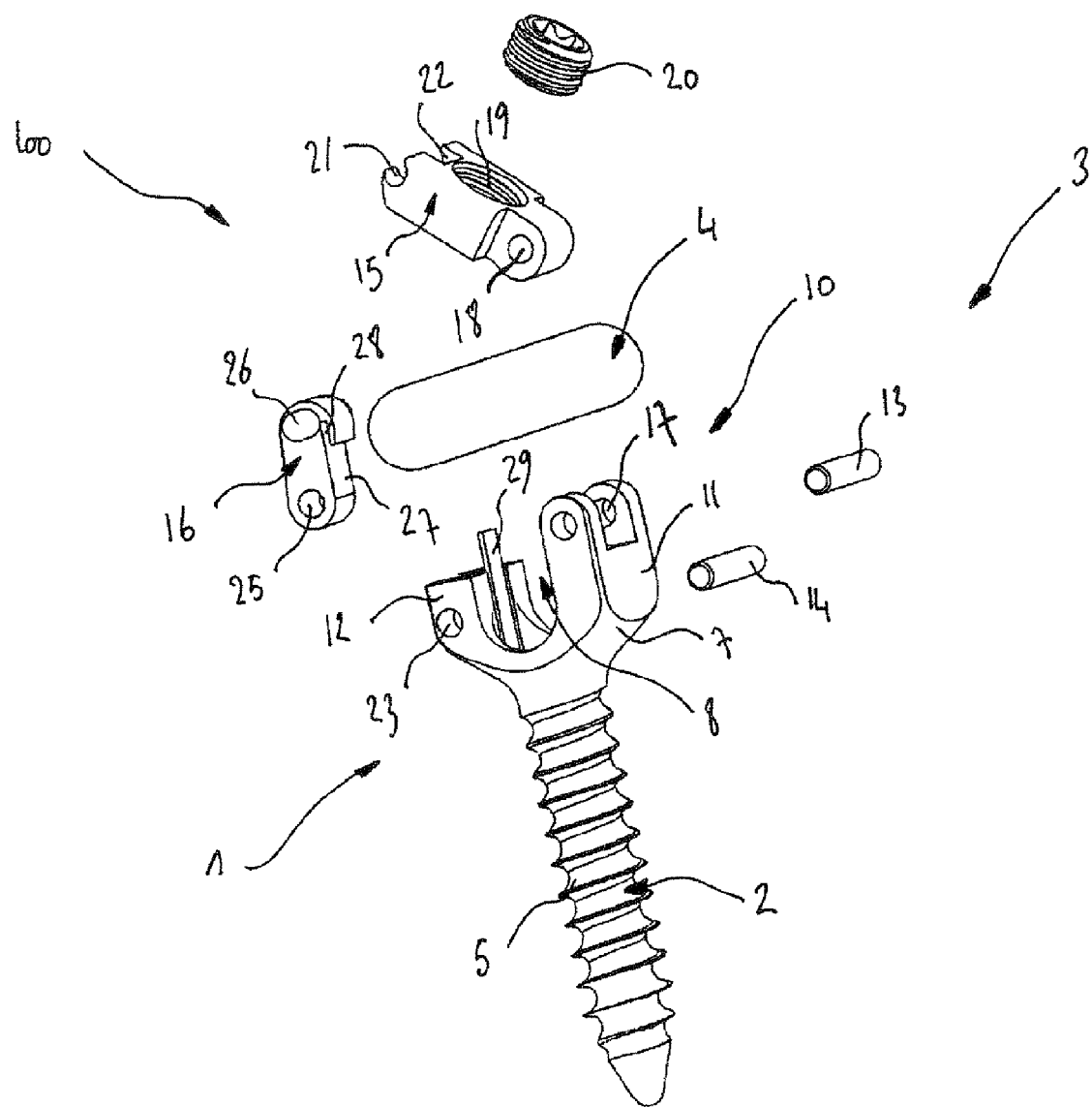
FIGS. 1 to 4 are perspective views illustrating the various elements constituting the hinge mounting system for a spinal osteosynthesis device according to the present invention.
Figure 2:
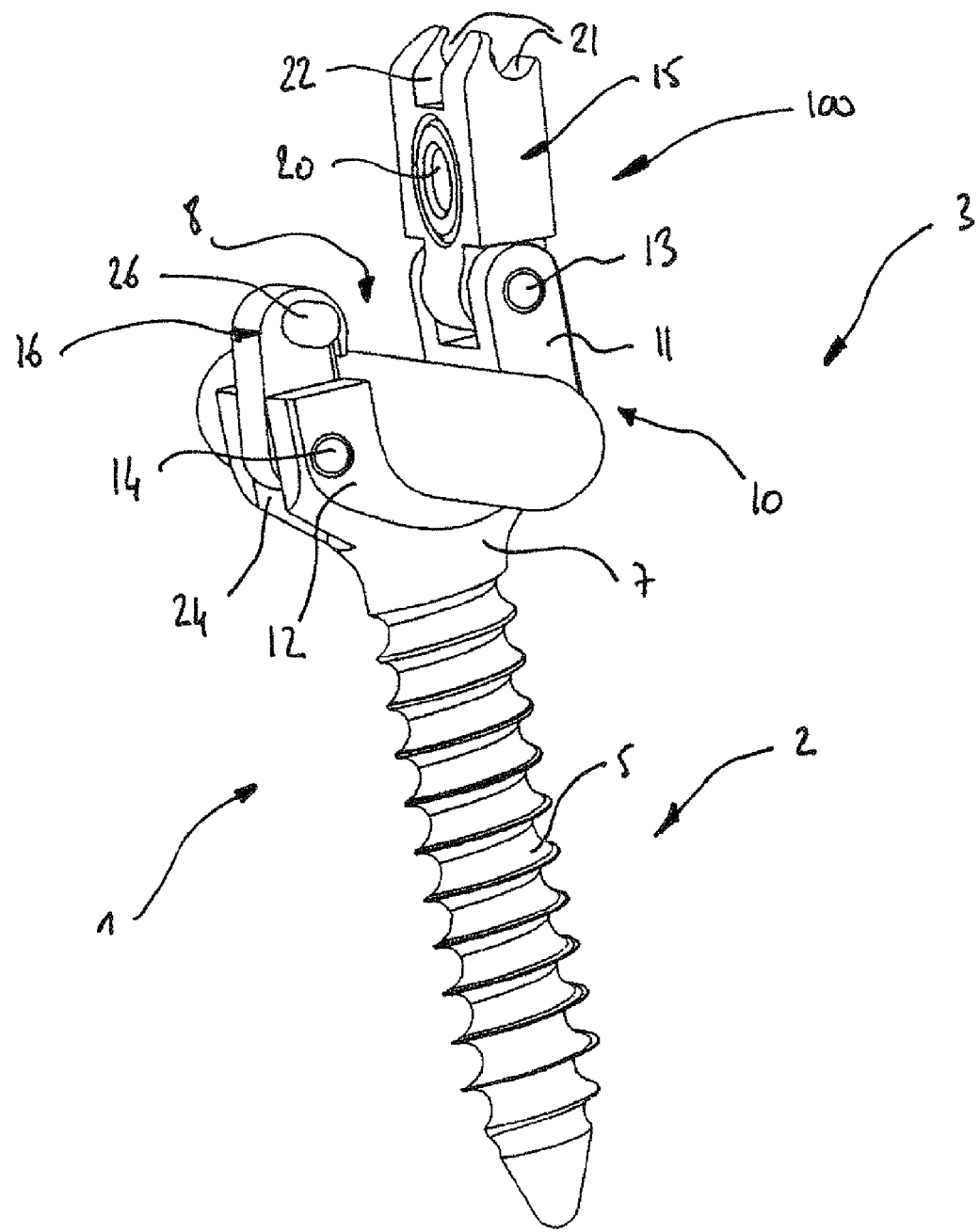
Figure 3:
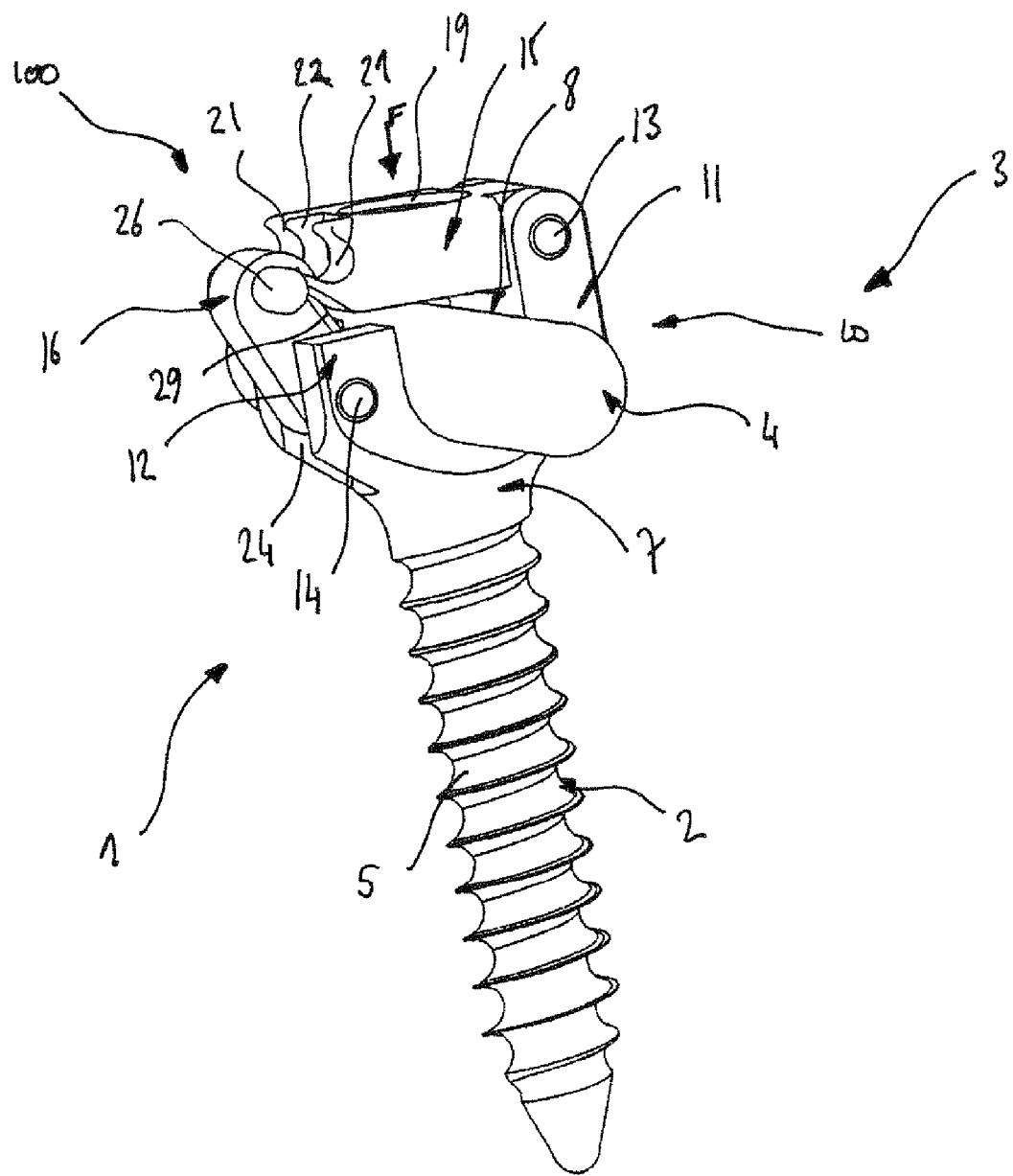
Figure 4:
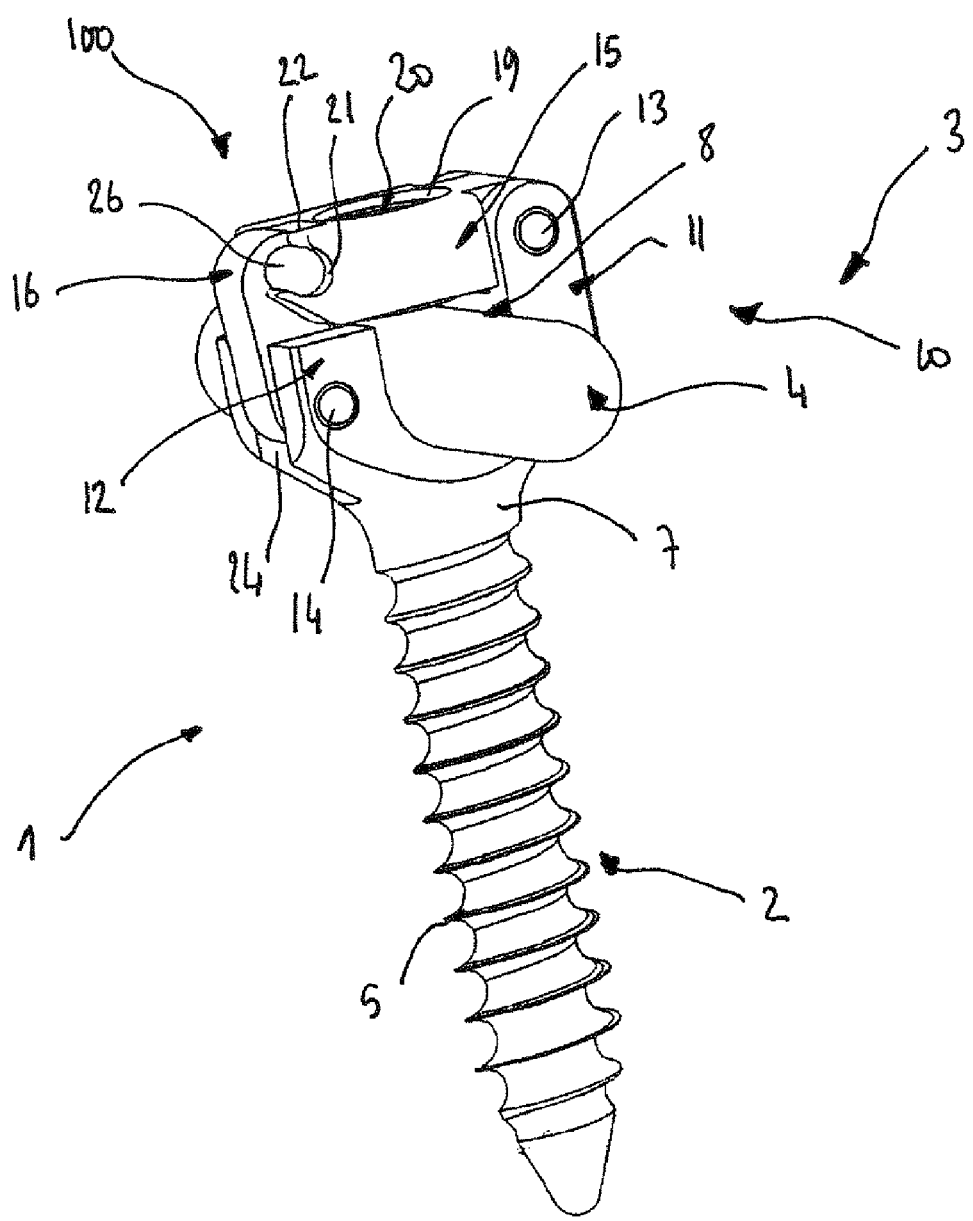

Anchoring screw 2 comprises, in the extension of its threaded part 5, a link connector 10 forming a connection head 7 equipped with a U-shaped opening 8 for the placement and passage of the linking rod 4.

The link connector 10 comprises, opposite from the bottom of the U-shaped opening 8, a hinge mounting system 100 allowing, after the system has been locked, the linking rod 4 to be clamped and immobilized in translation and in rotation in the bottom of said U-shaped opening 8.

The link connector 10 comprises, on either side of the U-shaped opening 8, a first and second vertical branch 11, 12 respectively allowing the assembly of a clamping element 15 and an elastically loaded lock 16 of the hinge mounting system 100 around an axis of rotation 13, 14.

The first branch 11 of the link connector 10 is pierced along a horizontal direction by a through bore 17 enabling, by means of the axis of rotation 13, the clamping element 15 to be mounted such that the latter may pivot around said axis of rotation 13 and close the U-shaped opening 8.

The clamping element 15 is pierced at one of its edges by a through hole 18 cooperating with the axis of rotation 13 during its assembly on the first branch 11 of link connector 10. The clamping element 15 is traversed in its middle along a direction perpendicular to that of hole 18 by a threaded bore 19 cooperating with a locking screw 20.

The clamping element 15 comprises, opposite the through hole 18 cooperating with the axis of rotation 13, an edge in which hook-shaped notches 21 are arranged, that are separated by a central vertical groove 22.

The second branch 12 of the link connector 10 comprises, on the one hand along a horizontal direction, a through hole 23, and on the other hand along a vertical direction, a groove 24 allowing the lock 16 to be placed and guided around the axis of rotation 14.

The groove 24 also enables the placement of a leaf spring 29 along a vertical direction wherein one of its ends is integral with connector 10 at the bottom of the U-shaped opening 8.

Lock 16, opposite bore 25 receiving axis of rotation 14, is integral with locking fingers 26 disposed along a direction parallel to that of said axis of rotation.

Lock 16 comprises, on one of its edges, and more particularly that edge oriented towards the U-shaped opening 8 of link connector 10, a vertical flat surface 27 that extends at the locking fingers 26 inside a groove 28 in order to guide and retain the free end of the leaf spring 29 opposite from the end that is integral with said link connector 10.

The leaf spring 29 enables lock 16 to be maintained in one and the same position, that is to say, along a direction that is vertical and parallel to that of said leaf spring 29, also known as the locking position.

It is noted that the axes of rotation 13 and 14, ensuring the pivoting of clamping element 15 and lock 16 on connector 10 of the hinge mounting system 100, are offset in relation to one another.

The operation of the hinge mounting system 100 according to the present invention is easily understood from the previous description.

In fact, when anchoring screw 2 is anchored in the bone of a vertebra and as the linking rod 4 is disposed in the bottom of the U-shaped opening 8 of the link connector 10, all the surgeon has to do is pivot the clamping element 15 so that the hooks 21 come in contact with the locking fingers 26 of the lock 16.

The surgeon applies vertical pressure F on clamping element 15 in order to push the lock 16 towards the outside of the link connector 10 in order to move apart said lock so that the locking fingers 26 of the latter may pass over hooks 21 of clamping element 15 and come, under the effect of the leaf spring 29, to be housed inside the latter.

Once the locking fingers 26 of lock 16 are housed in hooks 21 of clamping element 15, the surgeon withdraws the pressure F applied on said element 15. The clamping element 15 is thus retained above linking rod 4.

The surgeon then tightens locking screw 20 in order to immobilize the linking rod 4 in translation and in rotation inside the opening 8 of the link connector 10 of the corresponding osseous anchoring screw 2 of the spinal osteosynthesis device 3.

Figure 5:
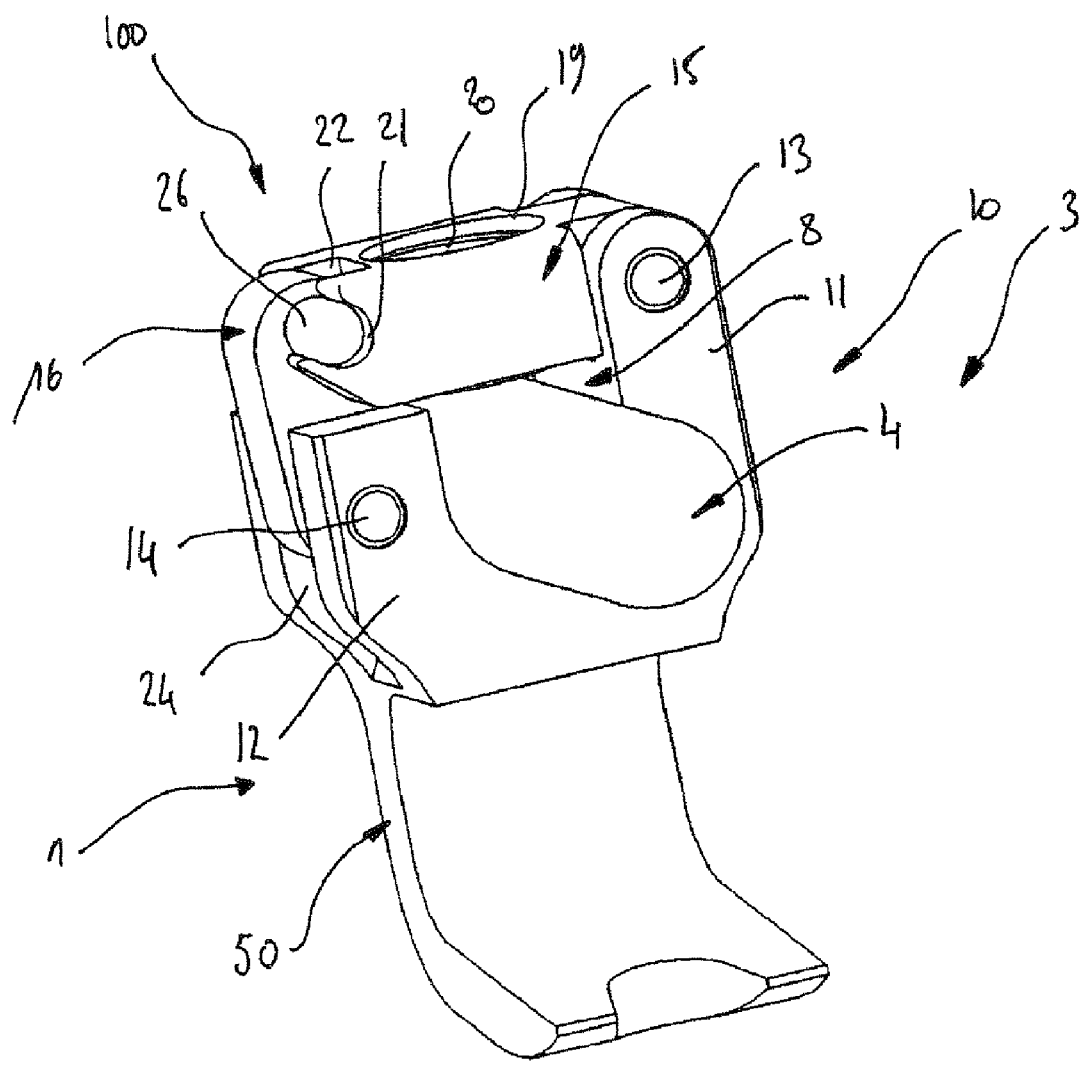
FIG. 5 is a perspective view representing, by way of a non-limiting example, another osseous anchoring means for a spinal osteosynthesis device on which the hinge mounting system according to the present invention is mounted.

FIG. 5 represents another osseous anchoring element 1 according to the present invention constituted, for example, of a hook 50 from a spinal osteosynthesis device 3 integral with the link connector 10 on which the hinge mounting system 100 is mounted for the fixation and immobilization in translation and in rotation of the linking rod 4 connecting various vertebral stages of a spinal segment of a vertebral column to be instrumented. The hook may be a pedicle, laminar or transverse hook.

Thus the hinge mounting system 100 according to the present invention may be provided on any type of osseous anchoring element such as, for example, the spherical head of an osseous anchoring screw so that the link connector 10 may pivot angularly around the latter before it is immobilized in a determined axial position.

The invention claimed is:

1. A hinge mounting system for an osseous anchoring element of a spinal osteosynthesis device enabling the immobilization in translation and in rotation of a linking rod connecting various vertebral stages of a spinal segment of a vertebral column to be treated, said system comprising:
    a link connector having first and second vertical branches on opposite sides of a U-shaped opening,
    a clamping element pivotally mounted on said first vertical branch to immobilize said linking rod in translation and in rotation, and
    a lock pivotally mounted on said second vertical branch and elastically loaded by a leaf spring,
    said clamping element and said lock having pivotal axes that are parallel to each other, said lock having a means for retaining said clamping element when said clamping element is swung into engagement with said linking rod.

2. The hinge mounting system according to claim 1, wherein said clamping element has a threaded bore in which is disposed a locking screw engageable with said linking rod to immobilize said linking rod in translation and in rotation.

3. The hinge mounting system according to claim 1, wherein said clamping element has a vertical groove having edges on opposite sides of said groove, and hook-shaped notches in said edges engageable with said means for retaining said clamping element to retain said clamping element in a locked position.

4. The hinge mounting system according to claim 1, wherein said second vertical branch has a vertical groove for receiving said lock, said leaf spring being secured to said second branch in said groove.

5. The hinge mounting system according to claim 4, wherein the lock has a vertical flat surface terminating in a groove in order to retain a free end of said leaf spring opposite from an end of said leaf spring secured to said link connector.

6. The hinge mounting system according to claim 1, wherein said means for retaining said clamping element comprises locking fingers disposed on opposite sides of said lock.

7. The hinge mounting system according to claim 1, wherein said axes of rotation of the clamping element and the lock are spaced from each other.

8. The hinge mounting system according to claim 1, wherein the link connector is integral with an osseous anchoring screw.

9. The hinge mounting system according to claim 1, wherein the link connector is integral with an osseous anchoring element comprising a hook.

* * * * *